(12) United States Patent
Lee et al.

(10) Patent No.: US 8,314,279 B2
(45) Date of Patent: Nov. 20, 2012

(54) PROCESS FOR SELECTIVELY MAKING OLEFINS FROM ENERGY DENSE ALCOHOLS

(75) Inventors: Ivan C. Lee, Silver Spring, MD (US); Douglas A. Behrens, Newark, DE (US)

(73) Assignee: The United States of America as reprensted by the Secretary of the Army, Washington, DC (US)

( * ) Notice: Subject to any disclaimer, the term of this patent is extended or adjusted under 35 U.S.C. 154(b) by 87 days.

(21) Appl. No.: 12/870,888

(22) Filed: Aug. 30, 2010

(65) Prior Publication Data

US 2012/0053384 A1    Mar. 1, 2012

(51) Int. Cl.
    *C07C 1/24*    (2006.01)
    *C07C 27/20*    (2006.01)
(52) U.S. Cl. .......................... 585/639; 518/703; 585/700
(58) Field of Classification Search .............. 518/703; 568/697, 895; 585/310, 446, 500, 639, 700
    See application file for complete search history.

(56) References Cited

U.S. PATENT DOCUMENTS

| | | | |
|---|---|---|---|
| 6,125,818 A | * | 10/2000 | Okamoto et al. ............. 123/305 |
| 6,566,573 B1 | | 5/2003 | Bharadwaj et al. |
| 2002/0087042 A1 | | 7/2002 | Schmidt et al. |
| 2006/0014840 A1 | | 1/2006 | Schmidt et al. |
| 2008/0131948 A1 | | 6/2008 | Manzer et al. |
| 2008/0132730 A1 | | 6/2008 | Manzer et al. |
| 2008/0132732 A1 | | 6/2008 | Manzer et al. |
| 2008/0234523 A1 | | 9/2008 | Manzer et al. |

OTHER PUBLICATIONS

Edward C. Wanat et al, "Partial oxidation of alcohols to produce hydrogen and chemicals in millisecond-contact time reactors," 235 Journal of Catalysis 18-27 (2005).
J.R. Salge et al, "Catalytic partial oxidation of ethanol over noble metal catalysts," 235 Journal of Catalysis 69-78 (2005).

* cited by examiner

*Primary Examiner* — Thuan D Dang
(74) *Attorney, Agent, or Firm* — John H. Raubitschek

(57) ABSTRACT

A process to perform selective catalytic oxidation of four-carbon alcohols to produce four-carbon olefins with yields greater than 90%. The process includes providing a supply of oxygen gas and a butanol fuel, atomizing and evaporating the fuel to produce a vapor, mixing the vapor with the oxygen to form a fuel mixture, reacting the fuel mixture in the presence of a heated solid $Rh/Al_2O_3$ or $Al_2O_3$ catalysts.

18 Claims, 8 Drawing Sheets

PROCESS FOR SELECTIVELY MAKING OLEFINS FROM ENERGY DENSE ALCOHOLS

GOVERNMENT INTEREST

The presently disclosed invention was made with U.S. Government support by the Army Research Laboratory. Thus, the United States Government has certain rights in the disclosed subject matter. The embodiments described herein may be manufactured, used, sold, imported and/or licensed by or for the United States Government without the payment of royalties.

BACKGROUND

The embodiments described herein relate to the selective catalytic combustion of butanol to make olefins in good yield.

Butanols are a desirable hydrocarbon source for energy and chemical industries mainly because they are easily available through fermentation of non-food biomass and wastewater. Dehydration of butanol isomers (including 1-butanol, 2-butanol and isobutanol) produce butenes (including 1-butene, cis-2-butene, trans-2-butene and isobutene) which are highly valuable starting materials for chemical industries to make synthetic fuels, lubricants and other high value chemicals. For examples, 1-butene is used in the creation of high density polyethylene as well as linear low density polyethylene. 2-butene is an extremely valuable starting material for lubricants as well as agricultural chemicals. In olefin metathesis, 2-butene reacts with ethylene to form propylene. Isobutene is the starting material for butyl rubber, methyl tert-butyl ether (MTBE), and isooctane. In addition, synthetic petroleum kerosene (SPK) can be synthesized by oligomerization of 4-carbon olefins. Unlike dehydration of butanol in the prior art, this invention is an oxidative process (i.e., combustion). The combustion of 1-butanol is extremely exothermic and occurs via Equation 1 shown below. This heat production enables the reaction to perform auto-thermally. As a result, the catalytic reaction is activated to reach an authermal reaction temperature of 330° C. to 600° C. when the reactant stream (butanol vapor and oxygen) is preheated at approximately 200° C. In contrast, traditional dehydration process requires external heating to maintain catalyst temperature at about 300° C. to 500° C.

$$CH_3CH_2CH_2CH_2OH + 6O_2 \rightarrow 4CO_2 + 5H_2O \quad \Delta H = -2713 \text{ kJ/mol} \quad (1)$$

In a combustion process, the equivalence ratio ($\phi$) of a system, defined herein as the ratio of the fuel-to-air/oxidizer ratio to the stoichiometric fuel-to-air/oxidizer ratio, plays an important role in fuel conversion. Mathematically, the equivalence ratio is represented as:

$$\phi = \frac{\text{fuel-to-oxidizer ratio}}{(\text{fuel-to-oxidizer ratio})_{st}} \quad (2)$$

$$= \frac{m_{fuel}/m_{ox}}{(m_{fuel}/m_{ox})_{st}}$$

$$= \frac{n_{fuel}/n_{ox}}{(n_{fuel}/n_{ox})_{st}}$$

where, m represents the mass, n represents number of moles, and suffix st stands for stoichiometric conditions.

The $\phi$-value can be controlled by adjusting the amounts of fuel and/or oxygen that are reacted. Having a $\phi$-value of unity (1) signifies a stoichiometric feed of fuel and air, as shown in the above equations. With reactions having high $\phi$-values (i.e., values ranging from 0.75 to 3), the reaction is considered "fuel rich" and incomplete combustion occurs because not enough oxygen exists to combust the fuel. However, reactions having low $\phi$-values (i.e., values ranging from 0 to 0.75) indicate reactions having a "fuel lean" environment with plenty of oxygen to oxidize the fuel into its combustion products: carbon dioxide and water.

The production of olefins from hydrocarbons is well known in the prior art. In particular, Patent Application Publication US2002/0087042 to Schmidt et al. teaches a process whereby ethane auto-thermally decomposes to form ethene. See also U.S. Pat. No. 6,566,573. However, this process only converts alkanes to mainly two and three carbon olefins, which are not as desirable as four carbon olefins to oligomerize into gasolines, jet fuels, diesel fuels or lubricants.

Patent Application Publications US 2008/0131948 and US 2008/0234523, both to Manzer et al., teach processes for converting dry and aqueous 2-butanol directly to isooctenes. However, these processes were carried out as batch processes, which are not favorable as a continuous flow reactor. Additionally, the butanol conversions were as high as 75%, but their selectivity into the desired iso-octenes was generally very low, which would create only a small product yield (yield=conversion×selectivity).

Patent Application Publications US 2008/0132730 and US 2008/0132732, both to Manzer et al., teach a process for producing butenes from dry and aqueous 2-butanol. In particular, US 2008/0132732 discusses achieving 100% conversion and 100% selectivity of a 70 wt % mixture of butanol. However, the reactions were carried out in a pressurized batch reactor (2 mL vials), making continual production impossible. Additionally, in US 2008/0132730, the selectivity and conversion of dry butanol was not as high, achieving only 75% conversion, and 100% selectivity. Both of these approaches used sulfuric acid (liquid) as the catalyst, which must then be separated from the liquid reactants, consequently adding another step. This implies frequent replacement of the catalyst, which would be expensive. These processes were also carried out in a pressurized batch reactor.

SUMMARY

In view of the foregoing, an embodiment herein provides a process for selectively converting four-carbon liquid alcohols to olefins, comprising providing a supply of oxygen gas, providing the alcohols, atomizing the alcohols, evaporating the alcohols to produce a fuel vapor, mixing the vapor with oxygen to form a fuel mixture, and reacting the fuel mixture in the presence of a solid heterogeneous catalysts of $Rh/Al_2O_3$ and/or $Al_2O_3$.

Additionally, the alcohols are selected from any one of pure 1-butanols, pure 2-butanols, and pure isobutanols.

The olefins produced comprise $C_4$ atoms with a selectivity of greater than 90% and a total conversion greater than 95%. Further, the olefins are selected from 1-butenes, cis-2-butenes, trans-2-butenes, and isobutenes.

Additionally, the alcohols are atomized by an electrostatic injection device through electrospray in any one of cone-jet mode, multi jet mode, and charge injection mode. Further, the alcohol droplets are evaporated by a heat tape on the outside of the reactor.

The alcohols have a flow rate of less than 10 milliliters per hour during electrospray and a pressure of less than 10 psig.

The process further includes adjusting operating conditions to selectively produce varying four-carbon olefins. Specifically, the operating conditions include a contact time of said fuel mixture with a catalyst, a temperature of the catalyst, and an equivalence ratio. Preferably, the contact time is in a range from about 145 ms to less than 550 ms, the temperature is in a range from about 330° C. to less than 600° C. and the equivalence ratio is in a range from about 0.15 to less than 18.

According to another embodiment herein provides a process to produce a butene product with a yield of 93% from a four carbon butanol-containing feed stream, the process comprising contacting the feed stream with a catalyst, consisting essentially of alumina monolith foam with Rh gamma-alumina, to produce the butene product. The reaction occurs in a continuous flow reactor operated at a temperature between about 330° C. to less than 600° C. Further, an equivalence ratio of the feed stream is in a range from about 0.15 to less than 18 and a contact time of the catalyst with the feed stream is in a range from about 145 ms to less than 550 ms.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1:
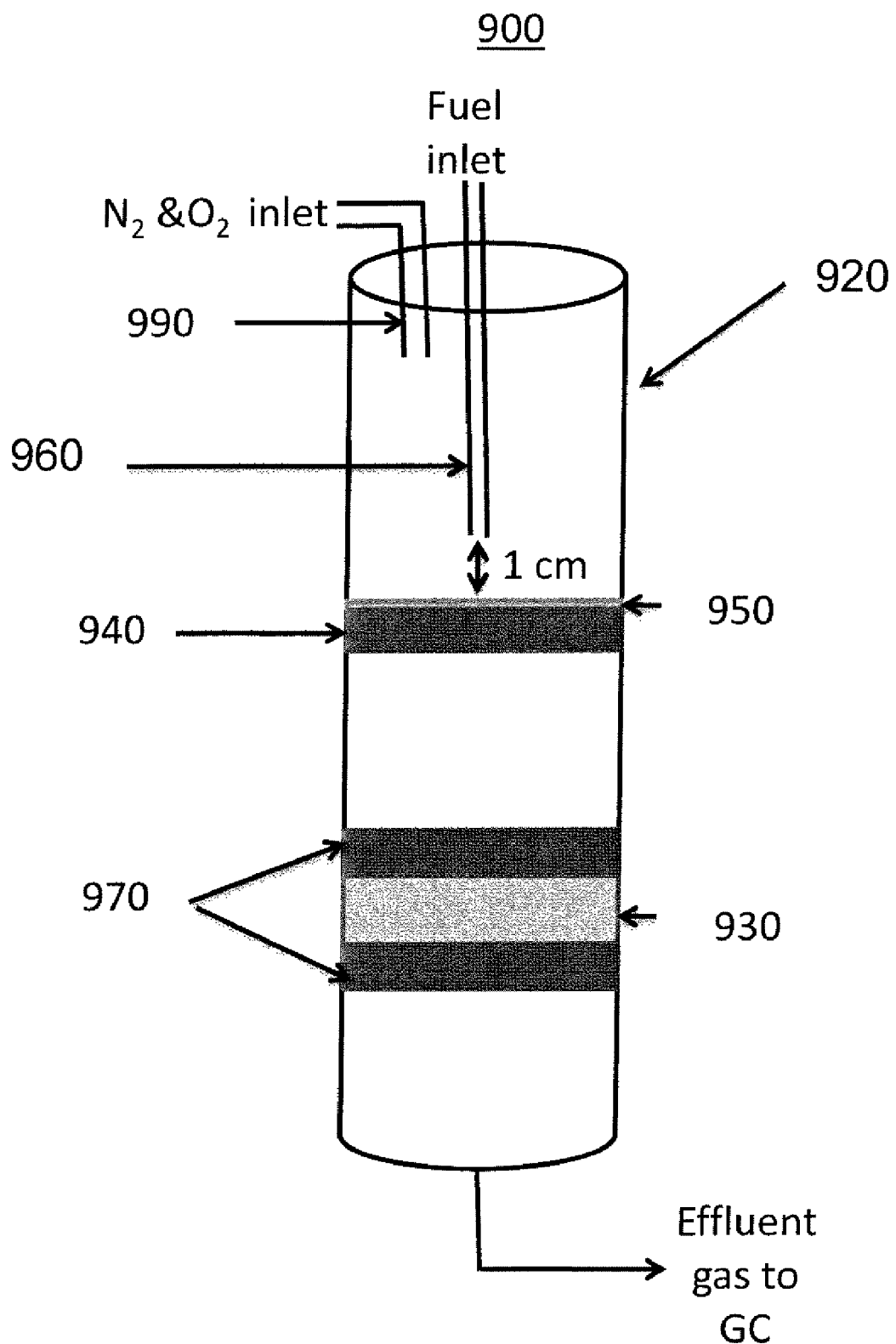
FIG. 1 illustrates a continuous flow reactor according to an embodiment described herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of ordinary skill in the art to practice the embodiments herein. Accordingly, the examples should not be construed as limiting the scope of the embodiments herein.

The embodiments described herein provide methods that include selective catalytic combustion and electrospray technologies to convert liquid butanol fuel in a continuous flow reactor to a variety of olefin products.

Referring now to the drawings, and more particularly to FIGS. 1 through 8, where similar reference characters denote corresponding features consistently throughout the figures, there are shown preferred embodiments.

FIG. 1 is an illustration of a continuous flow reactor according to an embodiment of the present invention. In particular, reactor 900 includes a quartz/ceramic wall 920, a grounded mesh or screen 950, a catalyst 930, foam mixing system 940, electrostatic fuel injection device 960 and gas intake 990.

It is to be appreciated, however, that the cylindrical shape of the reactor 900 may have alternative shapes and sizes. Following from the direction of gas intake 990, which for purposes of the embodiment described herein, is the top of the reactor 900, grounded mesh 950 is disposed below a droplet source (not shown) extending from and coupled to an electrostatic fuel injection device 960. Further, grounded mesh 950 is located at an approximate distance of 1 cm below the droplet source in order to have a large enough distance for the droplet to evaporate yet small enough distance to sustain the electrospray at a low voltage (e.g., 3500 V for single nozzle electrospray without an extractor electrode). Thus, the larger the distance between the droplet source and a grounded mesh, the more voltage or power that is needed. Pure oxygen gas or air is introduced through gas intake 990 and the effluent gas is released and sent to a gas chromatograph (GC) (not shown) through the bottom of the reactor 900. Additionally, liquid fuel is introduced into the stainless steel tube of the reactor 900 via a liquid pump (not shown). It is to be appreciated that the liquid fuel can include various types of energy dense fuels, including but not limited to butanols. Once introduced, the fuel is electrostatically atomized by creating a voltage difference between the droplet source and a grounded mesh 950 (e.g. 3500 V for single nozzle electrospray without an extractor electrode). Preferably, the fuel is electrosprayed using electrospraying techniques well known in the art, such as, for example, cone-jet mode, in order to ultimately assist with obtaining an optimum droplet size (e.g., 6 microns) and flow rate of less than 4 milliliters per hour per nozzle. Further, the electrospray injection device 960 requires minimal power of approximately 0.35 mW per nozzle. It is to be appreciated that other well known electrospraying techniques may be employed, such as, for example, multi jet mode, or charge injection, however, the present invention is not limited thereto.

The foam mixing system 940 is a layer of alumina located below the grounded mesh 950 to aid in the mixing of the fuel vapor and any incoming oxygen gas. Additionally, the grounded mesh 950 is perpendicular to the direction of the droplet trajectory in order to create an electric field between it and the electrostatic field injection device 960. Sufficient heat (e.g., less than 10 degrees above the boiling point of the fuel) was supplied via a heating tape on the outside of the reactor 900 to apply heat to the grounded mesh 950 to ensure complete evaporation or vaporization of the liquid fuel. The same heating tape also preheats the reactant stream (vaporized fuel and oxygen) to approximately 200° C. During start-up conditions, the pre-heating is achieved by the heating tape or an active heating element, while during operation, heat may be provided passively by heat reclamation processes. It is to be noted that any heating tape well known in the art may be utilized.

The catalyst material 930 is a solid material that is placed between two inert, porous alumina foams 970 that act as heat shields and also serve as an additional mixing layer to ensure uniform fuel vapor concentration over the entire catalyst surface. A foam catalyst containing either an $Al_2O_3$ foam or $Rh/Al_2O_3$ foam or both can be used as the catalyst which will be described in further detail below. For purposes of description, the $Rh/Al_2O_3$ foam (5 mm thick) contained 0.061 g of Rhodimum (Rh) and was prepared in a manner detailed in the text "Rhodimum Supported on Thermally Enhanced Zeolite as Catalysts for Fuel Reformation of Jet Fuels," Vol. 136 Catalysis Today p. 258-265 (2008) by Ivan C. Lee, which is incorporated herein by reference. The alumina monolith foam (80 pores per inch, 17 mm diameter, 5 mm thick) was coated with γ-alumina to roughen the foam surface and to increase the surface area. Then, the foam was calcined in a box furnace at 973 K for 15 hours. An aqueous $Rh(NO_3)_3$ solution was further added to the foam, and the resultant foam was calcined in the box furnace at approximately 973 K for a subsequent 15 hours. The contact time between the catalyst, fuel, and oxygen as well as the flow rate is dependent upon the thickness of the catalyst. That is, the thicker the catalyst material or smaller the flowrate, the greater the increase in contact time. Thus, as expressed in a formula, contact time=thickness (of the catalyst material)/flow rate.

Next, a general explanation of the converted products will be given in further detail according to experiments conducted with reference to the embodiments of the invention. This explanation is intended to be illustrative of the invention but is not meant to be construed as limiting the reasonable scope of the invention.

Figure 2:
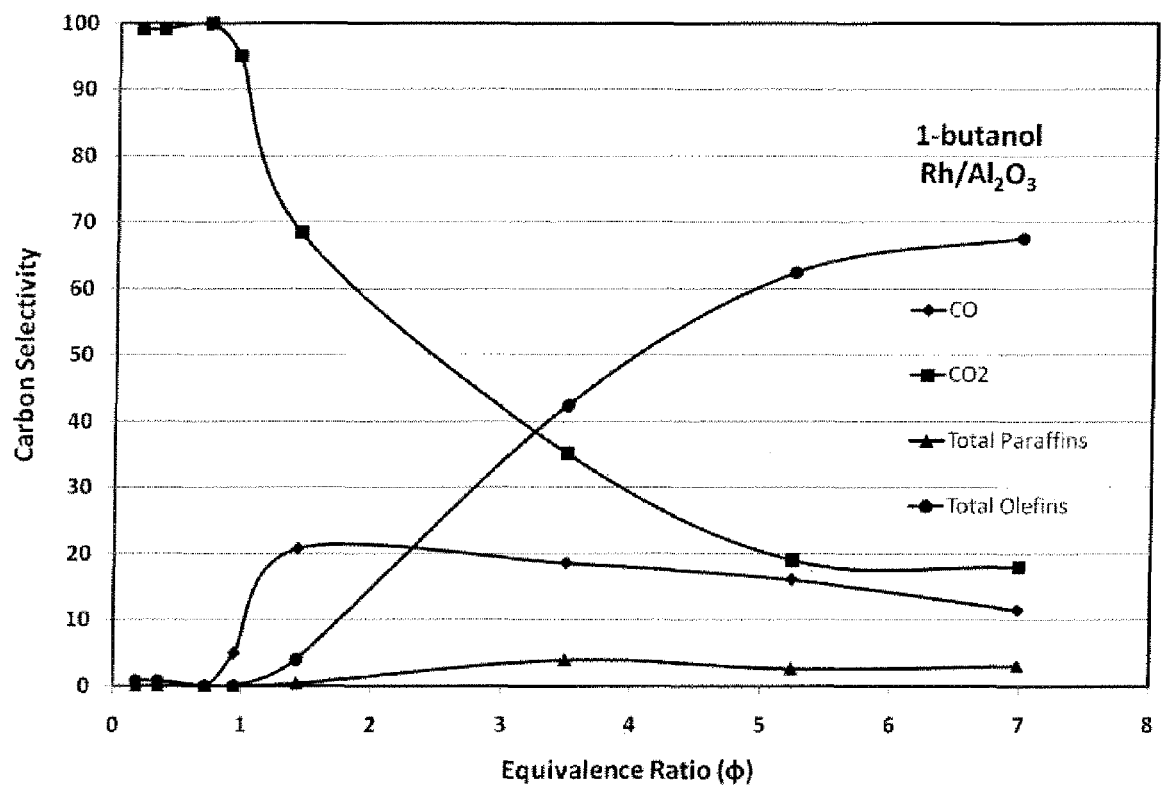
FIG. 2 illustrates a graphical representation of the carbon selectivity for 1-butanol reactions using a $Rh/Al_2O_3$ catalyst.

An air tight seal was placed around the reactor 900 and the GC (not shown). The amounts of hydrogen, oxygen, nitrogen, carbon monoxide, carbon dioxide, methane, acetylene, ethane, ethylene, propane, propylene, butane, 1-butene, isobutene, cis-2-butene, and trans-2-butene were monitored by an Agilent 4-channel micro-GC (not shown). Before each new iteration of fuel intake, nitrogen was first passed through the reactor 900 in order to clear out any lingering gases, to ensure that no leaks existed, and to ensure that no residual oxygen was present. After the appropriate nitrogen and oxygen flow rates were introduced according to the contact time and equivalence ratio, the grounded mesh 950 and catalyst 930 temperatures were allowed to equilibrate. Typical steady state temperature of the ground mesh 950 is about 2-10° C. above the boiling point of the specific butanol. When the fuel flow is introduced (atomized and vaporized), chemical reaction occurs on the catalyst 930. As a result, the catalyst 930 temperature rises. The catalyst 930 temperatures were again allowed to reach a steady state operating autothermal temperature (e.g. ranging from 330° C. to 600° C.) and the GC recorded the gas composition during this time. The overall contact time of the catalyst 930 with the fuel, nitrogen and oxygen ranged between 145 ms to 550 ms. The equivalence ratio $\phi$ was varied utilizing both the $Rh/Al_2O_3$ and $Al_2O_3$ foam catalysts, ranging from 0.18-18, thereby providing different products with three distinct regimes. For example, as shown in FIG. 2, in 1-butanol combustion utilizing the $Rh/Al_2O_3$ foam catalyst, for the equivalence ratio $\phi<1$, carbon dioxide and water were selectively produced (i.e., with 100% carbon selectivity, a conversion >95%, and a yield >95%). Additionally, under the same conditions, hydrogen and carbon monoxide yields were minimal. It is to be noted that selectivity is defined herein as how many atoms are converted to some other product and yield is expressed as conversion× selectivity which will be discussed in further detail below.

The fuel conversion was determined by analyzing exhaust gas composition with the flame ionization detector of a second GC. A HP-INNOWAX column was employed to quantify polar molecules including 1-butanol, 2-butanol, isobutanol, methanol, acetone, and acetaldehyde wherein conversion is defined by:

$$\text{Conversion} = 1 - \frac{\text{amount of remaining butanol}}{\text{original amount of butanol}} \quad (3)$$

The carbon selectivity was defined as the number of carbon atoms in a product species, divided by the total number of carbon atoms in all the product species. Hydrogen selectivity was defined in an analogous way, and the definition of carbon selectivity is shown in Equation 4 below. In particular, $$\text{Carbon Selectivity} = \frac{\text{\# } C \text{ in Species } X}{\Sigma \, C \text{ in product}} \quad (4)$$

FIGS. 2-7 illustrate the carbon selectivity of the combustion products of 1-butanol, 2-butanol and isobutanol with $Al_2O_3$ or $Rh/Al_2O_3$ catalyst. The Table below describes the carbon selectivities for individual olefins that were produced by the combustion of various butanols. Equilibrium calculations of 1-butanol combustion indicate that methane, carbon monoxide and carbon dioxide are the major carbon-containing species at high $\phi$. The amount of olefins in the equilibrium mixture is negligible. In contrast, the experimental data with $Al_2O_3$ or $Rh/Al_2O_3$ in short contact time (150 ms) indicated that olefins were produced at high $\phi$ ($\phi>3.5$). The data suggest contact time of 150 ms is too short to achieve equilibrium composition. As a result, a non-equilibrium product mixture with butenes is produced in the short contact time during the combustion of butanols.

Figure 3:
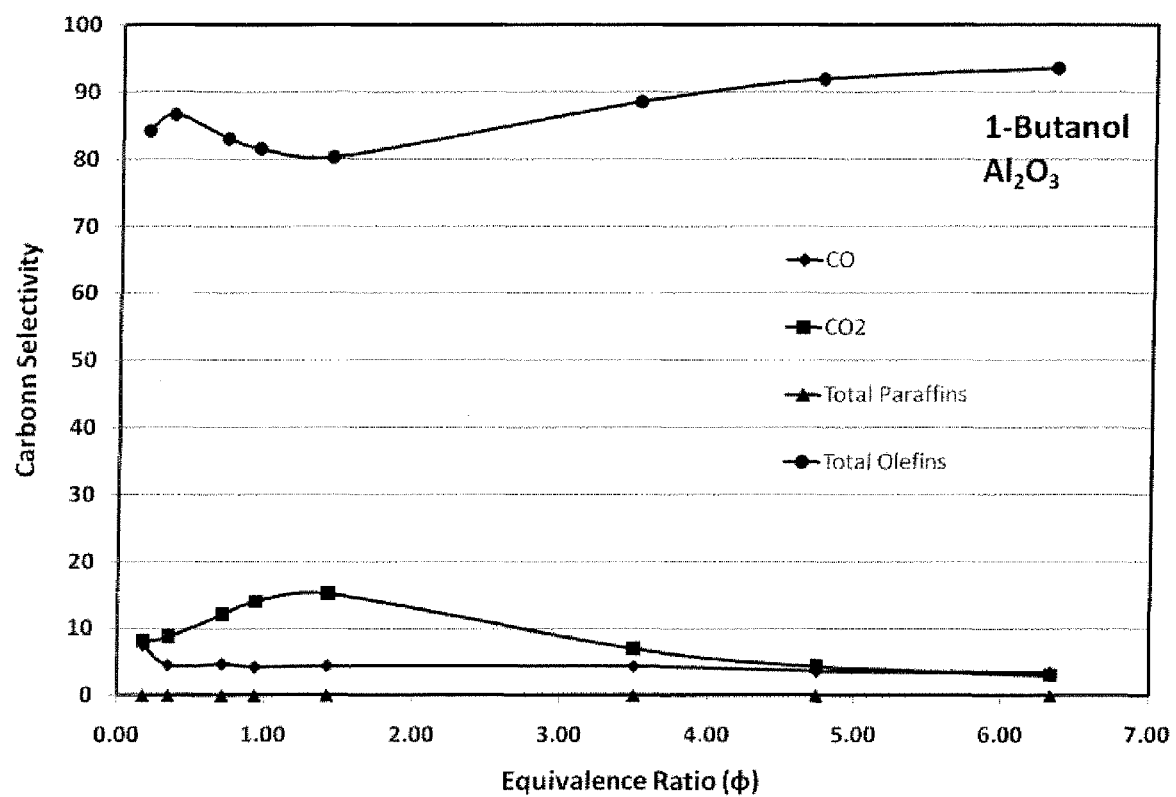
FIG. 3 illustrates a graphical representation of the carbon selectivity for 1-butanol reactions using an $Al_2O_3$ catalyst.

FIGS. 2 and 3 illustrate the carbon selectivity of 1-butanol combustion products utilizing the $Rh/Al_2O_3$ and $Al_2O_3$ catalyst, respectively. It is shown that three distinct regimes exist in presence of Rh, and that the fuel combustor can be tuned to operate in any regime by changing $\phi$ (FIG. 2). In particular, increasing the $\phi$ reduces the relative amount of $O_2$ present in the feed. When the equivalence ratio is less than 1, complete combustion occurs with the formation of $H_2O$ and $CO_2$ as the major products. The carbon selectivity of carbon monoxide continues to increase for $\phi$ values up to 1.57. At $\phi=3.5$, the carbon selectivity of propylene, 1-butene, trans-2-butene and cis-2-butene were 14.0, 15.5, 6.3 and 6.6, respectively. As the $\phi$ increased to 6.99, the selectivity of 1-butene increased to 36.4% while carbon selectivity of propylene, trans-2-butene and cis-2-butene only changed slightly. In contrast, there is only olefin production regime in the absence of Rh (FIG. 3). The amount of olefin did remain high for $0.17<\phi<6.4$. The major olefins were 1-butene, cis-2-butene, trans-2-butene. At $\phi=6.3$, the carbon selectivity of 1-butene, cis-2-butene and trans-2-butene were 64.4%, 14.1% and 10.6, respectively. Meanwhile, the amount of propylene is negligible. $Rh/Al_2O_3$ catalyst enhances the conversion of 1-butanol to CO and $CO_2$ when compared to $Al_2O_3$ catalyst. Therefore, $Al_2O_3$ is the preferred catalyst for 1-butene production from 1-butanol.

Figure 4:
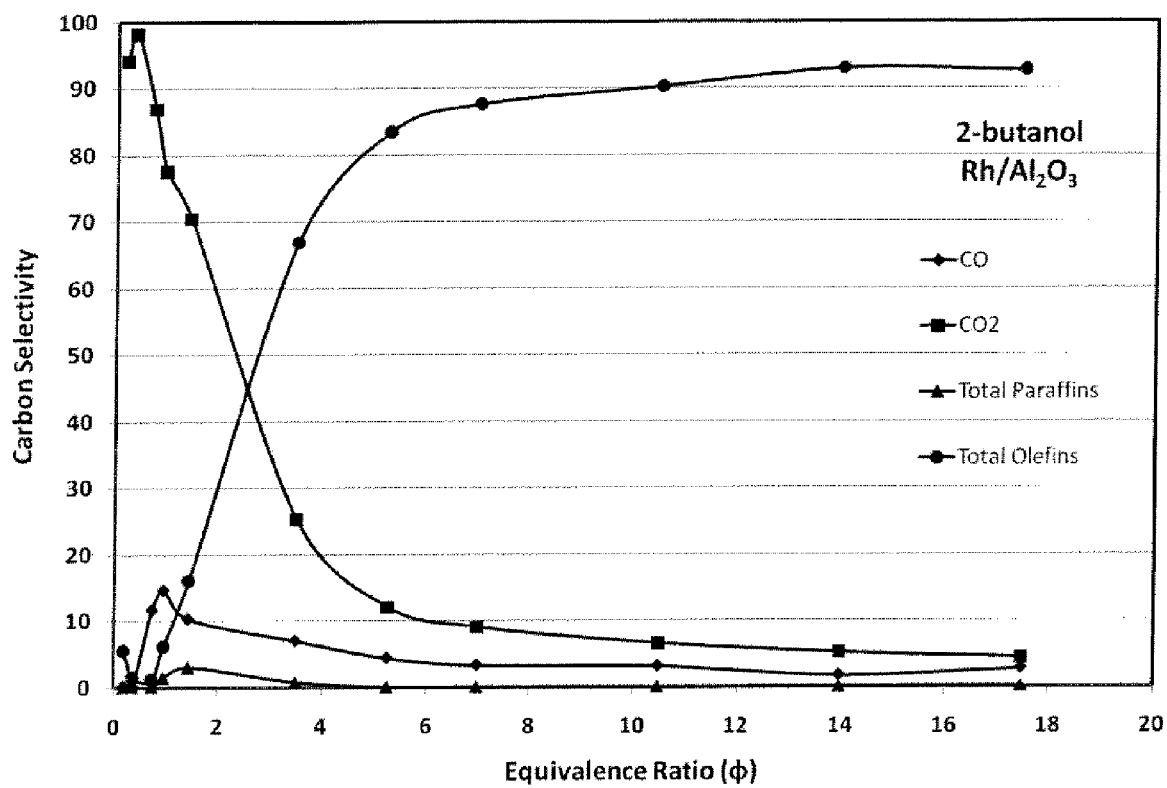
FIG. 4 illustrates a graphical representation of the carbon selectivity for 2-butanol reactions using a $Rh/Al_2O_3$ catalyst.
Figure 5:
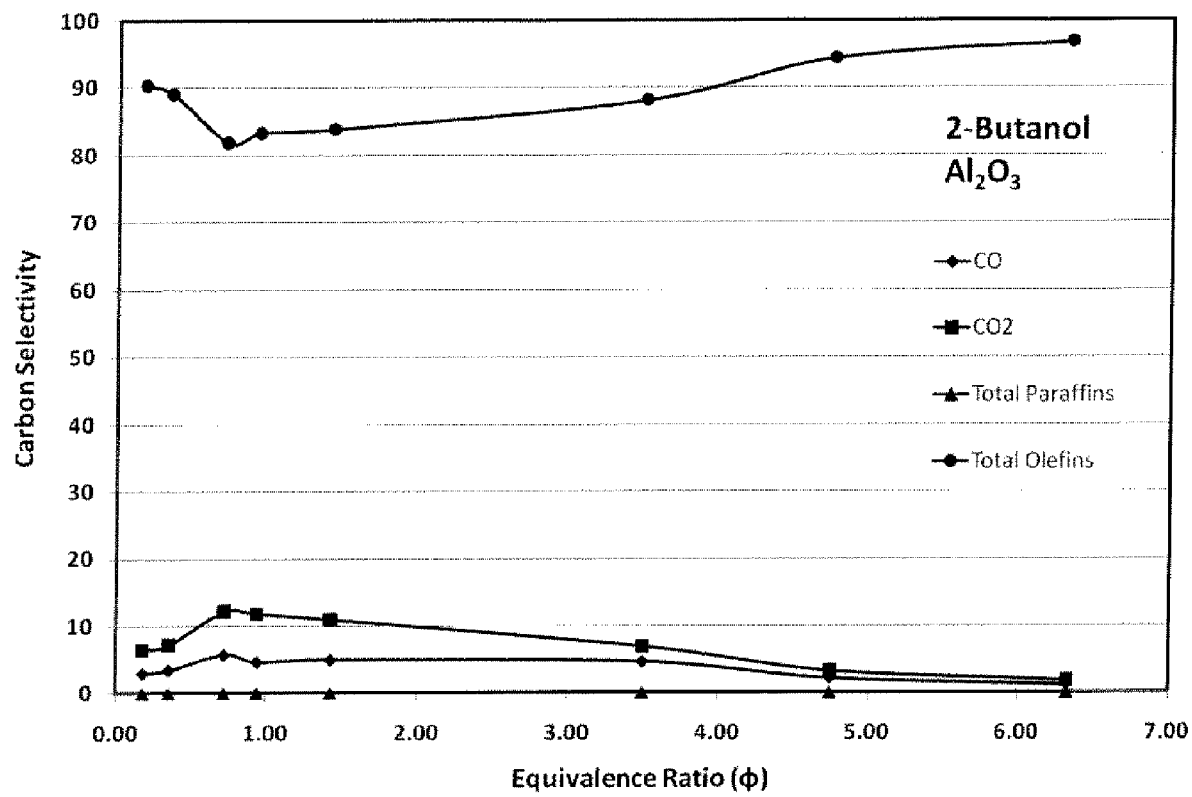
FIG. 5 illustrates a graphical representation of the carbon selectivity for 2-butanol reactions using an $Al_2O_3$ catalyst.

Referring to FIGS. 4 and 5, the graphical representations of the carbon selectivity for 2-butanol combustion products with $Rh/Al_2O_3$ and $Al_2O_3$ catalysts are shown. Like combustion of 1-butanol, there are 3 distinct regimes in presence of Rh (FIG. 4). Complete combustion occurs for equivalence ratios less than 1, and almost 100% of the carbons are found in carbon dioxide. At $\phi=1$, the selectivity of carbon monoxide rises as that of carbon dioxide decreases. Finally, for $\phi>10$, olefin production becomes prominent as nearly 90% of the carbons leave the reactor as an olefin. The major olefin products were 1-butene, cis-2-butene and trans-2-butene. At $\phi=6.99$, the carbon selectivity of 1-butene, cis-2-butene and trans-2-butene were 25.1%, 35.8% and 26.2%, respectively. At $\phi=17.5$, the carbon selectivity of 1-butene, cis-2-butene and trans-2-butene were 27.4%, 38.8% and 25.9%, respectively. At these equivalence ratios, the 2-butene (including cis- and trans-) are produced with over 50% selectivity. In absence of Rh, there is only olefin production regime (FIG. 5). The major olefin products were 1-butene, cis-2-butene and trans-2- butene. At ϕ=6.33, the carbon selectivity of 1-butene, cis-2-butene and trans-2-butene were 35.2%, 35.8% and 25.3%, respectively. Therefore, both $Rh/Al_2O_3$ an $Al_2O_3$ produce 2-butenes (including cis- and trans-) as the preferred olefins. In particular, $Rh/Al_2O_3$ is the preferred catalyst for cis-2-butene production from 2-butanol.

Figure 6:
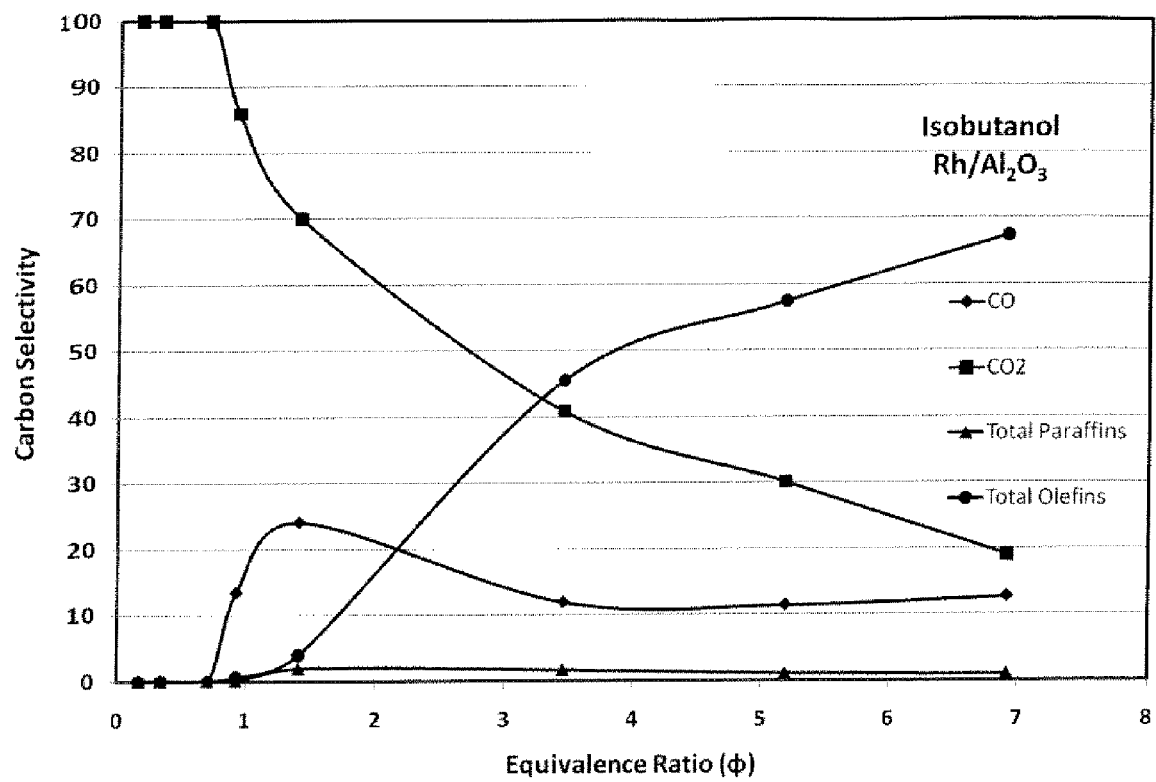
FIG. 6 illustrates a graphical representation of the carbon selectivity for isobutanol reactions using a $Rh/Al_2O_3$ catalyst.
Figure 7:
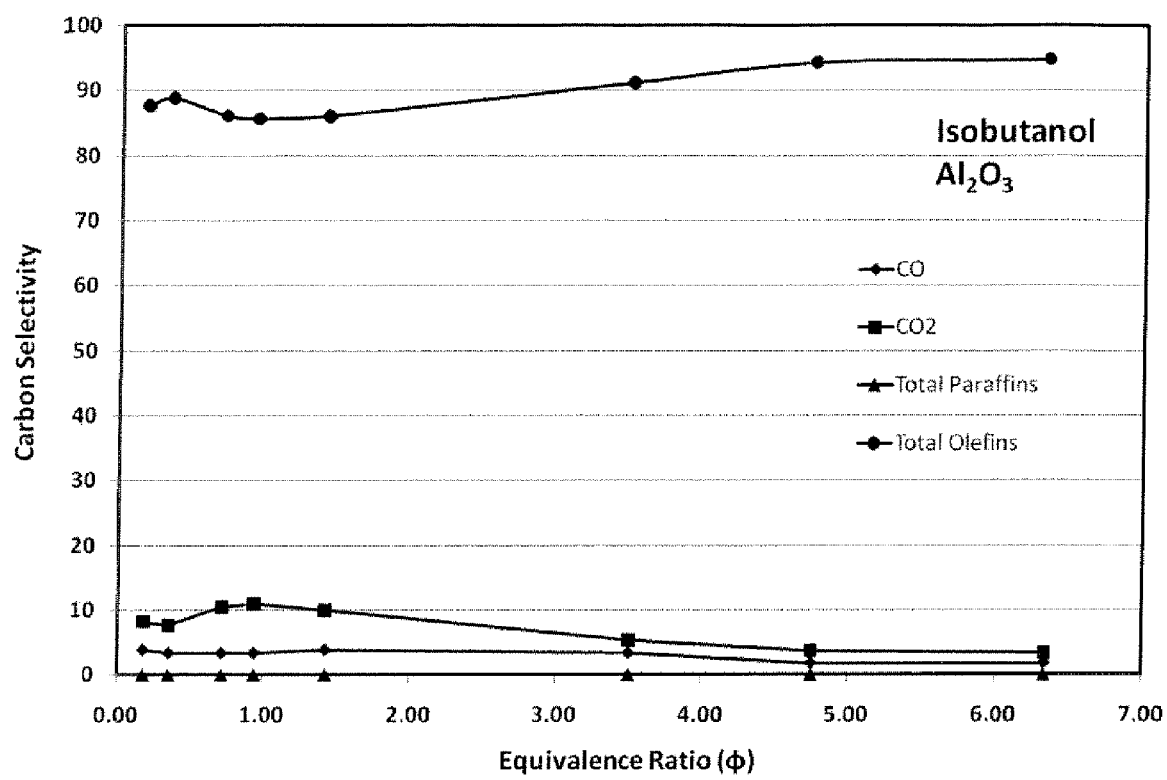
FIG. 7 illustrates a graphical representation of the carbon selectivity for isobutanol reactions using an $Al_2O_3$ catalyst.

FIGS. 6 and 7 illustrate the carbon selectivity of isobutanol combustion products utilizing the $Rh/Al_2O_3$ and $Al_2O_3$ catalyst, respectively. Like combustion of 1-butanol, there are 3 distinct regimes in presence of Rh (FIG. 5). Olefin production becomes the dominant pathway when ϕ>3.46. At ϕ=3.46, the major olefin products are propylene and isobutene with carbon selectivity of 24.7% and 17.7%, respectively. When the equivalence ratio is further increased to 6.92, more isobutene was produced and selectivity of propylene dropped. At this equivalence ratio (ϕ=6.92), the carbon selectivity of propylene and isobutene are 16.2% and 39.3%, respectively. Unlike with 1-butanol or 2-butanol, only very small amounts of 1-butene, cis-2-butene, and trans-2-butene were produced (with selectivities <5%) with isobutanol. Additionally, isobutanol produced mainly isobutene, (with selectivity of about 40%), whereas 2-butanol produced no isobutene. This demonstrated that there is a preferred reaction pathway that results in the formation of isobutene. Using an $Al_2O_3$ catalyst, olefin production dominates for ϕ between 0.18 to 6.34 (FIG. 7). The only major product of olefin is isobutene. At ϕ=6.34, the carbon selectivity of isobutene is 74.2%. Therefore, $Al_2O_3$ is the preferred catalyst for isobutene production from isobutanol.

Figure 8:
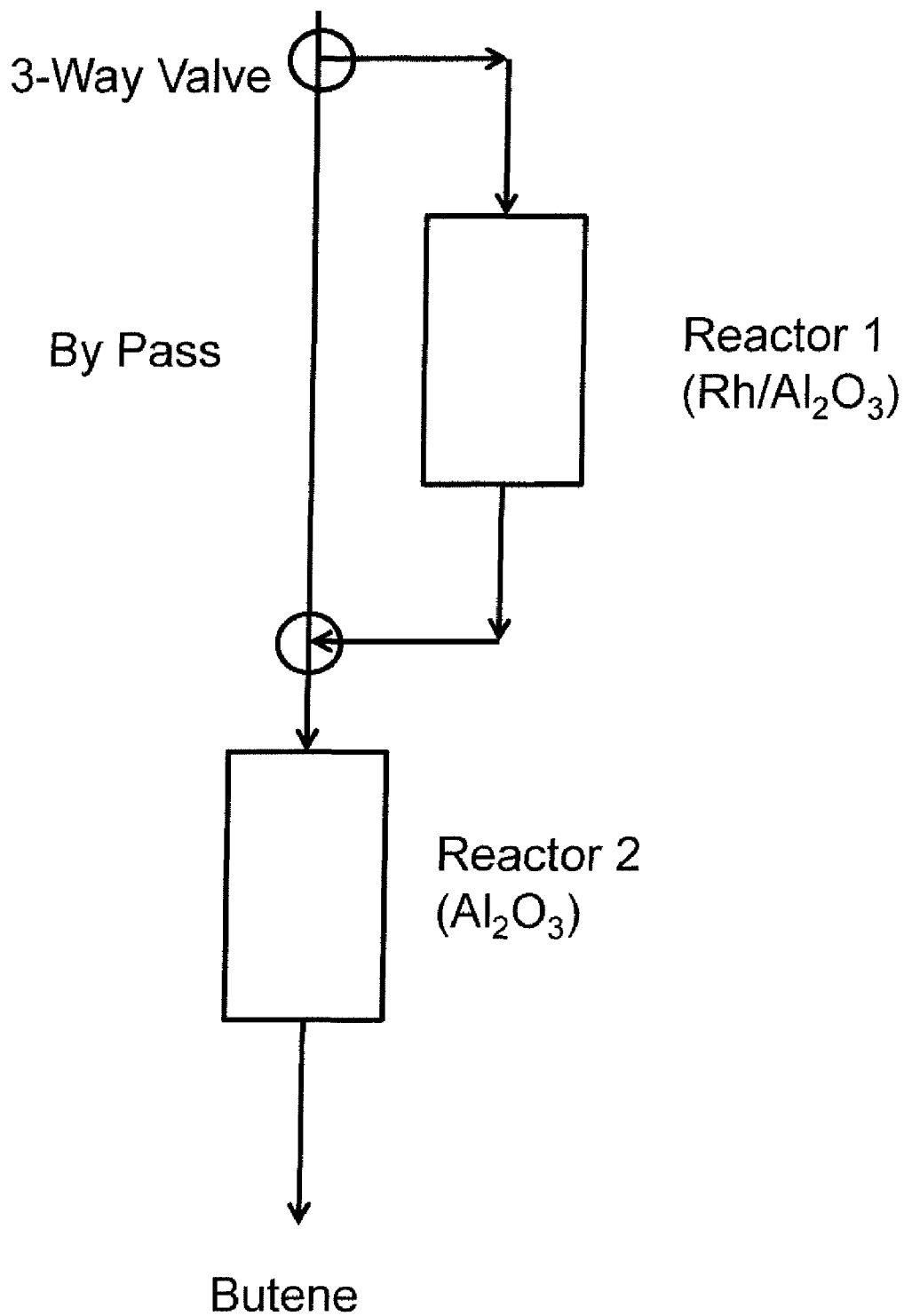
FIG. 8 illustrates a schematic diagram of combining two continuous flow reactors with $Rh/Al_2O_3$ and $Al_2O_3$ catalysts.

The 3-regime operation of $Rh/Al_2O_3$ catalyst for combustion of butanol isomers (1-butanol, 2-butanol and isobutanol) is beneficial to provide hot combustion gas to regenerate the reactor with $Al_2O_3$ catalyst. One possible schematic process diagram is shown in FIG. 8, where $Rh/Al_2O_3$ and $Al_2O_3$ catalysts may both be used. It is very common for a reactor to become less efficient as it ages. Catalyst fouling with carbon deposit is one of the main causes for such aging. FIGS. 2, 4 and 6 demonstrate that complete combustion of butanol occurs when ϕ<1. Therefore, one can feed the butanol to the reactor with $Rh/Al_2O_3$ to generate hot gas ($CO_2$ and water) with excess oxygen. This hot mixture passes to the fouled reactor with $Al_2O_3$ as catalyst during the regeneration process. Alternatively, cis-2-butene production with $Rh/Al_2O_3$ catalyst can be self-regenerated by changing the equivalence ratio. In summary, the total selectivities for 1-butanol and isobutanol are almost identical over the range of equivalence ratios studied. However, 2-butanol produces olefins with a much higher selectivity for all equivalence ratios larger than 2. If total olefins are what is desired, then 2-butanol has the advantage, but if a particular butene is desired, then 1-butanol or isobutanol would be the better choice because they selectively produce one butene rather than multiple butenes.

Lastly, the multi-regime capability of $Rh/Al_2O_3$ provides an additional advantage. During catalyst regeneration, the Rh acts as combustion catalyst to combust the carbon deposit on the catalyst by running ϕ<1.

TABLE

| Expt | Catalyst | Contact Time | Fuel | Phi | propylene | 1-butene | trans-2-butene | cis-2-butene | isobutene | Total Olefins |
|---|---|---|---|---|---|---|---|---|---|---|
| 1 | Rh/Al2O3 | 156 | 1-butanol | 3.49 | 14.0 | 15.5 | 6.3 | 6.6 | 0.0 | 42.4 |
| 2 | Rh/Al2O3 | 156 | 1-butanol | 5.24 | 10.9 | 30.8 | 9.8 | 10.9 | 0.0 | 62.5 |
| 3 | Rh/Al2O3 | 156 | 1-butanol | 6.99 | 13.3 | 36.4 | 8.0 | 9.4 | 0.0 | 67.6 |
| 4 | Al2O3 | 151 | 1-butanol | 0.18 | 1.5 | 55.3 | 11.7 | 15.6 | 0.0 | 84.2 |
| 5 | Al2O3 | 151 | 1-butanol | 0.35 | 1.6 | 57.4 | 11.7 | 15.9 | 0.0 | 86.6 |
| 6 | Al2O3 | 151 | 1-butanol | 0.72 | 1.6 | 55.7 | 10.9 | 14.9 | 0.0 | 83.0 |
| 7 | Al2O3 | 151 | 1-butanol | 0.94 | 1.4 | 56.0 | 10.1 | 14.0 | 0.0 | 81.5 |
| 8 | Al2O3 | 151 | 1-butanol | 1.43 | 1.7 | 55.4 | 9.6 | 13.5 | 0.0 | 80.2 |
| 9 | Al2O3 | 151 | 1-butanol | 3.50 | 2.0 | 61.5 | 10.6 | 14.5 | 0.0 | 88.5 |
| 10 | Al2O3 | 151 | 1-butanol | 4.75 | 1.8 | 64.4 | 10.9 | 14.8 | 0.0 | 91.9 |
| 11 | Al2O3 | 151 | 1-butanol | 6.34 | 2.6 | 64.4 | 10.6 | 14.1 | 0.0 | 93.5 |
| 12 | Rh/Al2O3 | 156 | 2-butanol | 1.42 | 0.0 | 3.8 | 5.2 | 7.1 | 0.0 | 16.1 |
| 13 | Rh/Al2O3 | 156 | 2-butanol | 3.49 | 0.4 | 16.3 | 20.6 | 29.5 | 0.0 | 67.0 |
| 14 | Rh/Al2O3 | 156 | 2-butanol | 5.24 | 0.5 | 23.5 | 25.6 | 33.9 | 0.0 | 83.6 |
| 15 | Rh/Al2O3 | 156 | 2-butanol | 6.99 | 0.5 | 25.1 | 26.2 | 35.8 | 0.0 | 87.7 |
| 16 | Rh/Al2O3 | 150 | 2-butanol | 10.48 | 0.5 | 26.3 | 26.4 | 37.1 | 0.0 | 90.3 |
| 17 | Rh/Al2O3 | 150 | 2-butanol | 13.98 | 0.5 | 27.7 | 25.9 | 38.9 | 0.0 | 93.1 |
| 18 | Rh/Al2O3 | 150 | 2-butanol | 17.47 | 0.6 | 27.4 | 25.9 | 38.8 | 0.0 | 92.8 |
| 19 | Al2O3 | 156 | 2-butanol | 0.18 | 1.5 | 32.5 | 25.0 | 29.6 | 1.8 | 90.4 |
| 20 | Al2O3 | 156 | 2-butanol | 0.35 | 1.4 | 31.9 | 24.9 | 30.1 | 0.9 | 89.2 |
| 21 | Al2O3 | 156 | 2-butanol | 0.72 | 1.1 | 30.0 | 23.4 | 27.4 | 0.0 | 81.9 |
| 22 | Al2O3 | 156 | 2-butanol | 0.94 | 1.0 | 30.7 | 23.5 | 28.3 | 0.0 | 83.4 |
| 23 | Al2O3 | 156 | 2-butanol | 1.42 | 0.9 | 30.9 | 23.6 | 28.5 | 0.0 | 83.9 |
| 24 | Al2O3 | 156 | 2-butanol | 3.50 | 0.1 | 32.6 | 24.8 | 30.8 | 0.0 | 88.2 |
| 25 | Al2O3 | 156 | 2-butanol | 4.75 | 0.5 | 34.2 | 25.4 | 34.4 | 0.0 | 94.5 |
| 26 | Al2O3 | 156 | 2-butanol | 6.33 | 0.6 | 35.2 | 25.3 | 35.8 | 0.0 | 96.9 |
| 27 | Rh/Al2O3 | 150 | isobutanol | 3.46 | 24.7 | 1.0 | 0.9 | 1.2 | 17.7 | 45.6 |
| 28 | Rh/Al2O3 | 150 | isobutanol | 5.19 | 18.5 | 2.1 | 1.8 | 2.5 | 32.5 | 57.4 |
| 29 | Rh/Al2O3 | 150 | isobutanol | 6.92 | 16.2 | 4.2 | 3.2 | 4.4 | 39.3 | 67.4 |
| 30 | Al2O3 | 156 | isobutanol | 0.18 | 2.8 | 9.6 | 4.5 | 6.1 | 64.7 | 87.7 |
| 31 | Al2O3 | 156 | isobutanol | 0.35 | 2.3 | 9.8 | 4.5 | 6.2 | 66.1 | 88.8 |
| 32 | Al2O3 | 156 | isobutanol | 0.72 | 1.7 | 9.2 | 4.3 | 5.9 | 65.1 | 86.1 |
| 33 | Al2O3 | 156 | isobutanol | 0.94 | 1.6 | 9.1 | 4.2 | 5.8 | 64.9 | 85.7 |
| 34 | Al2O3 | 156 | isobutanol | 1.42 | 1.5 | 9.4 | 4.4 | 5.9 | 65.0 | 86.1 |
| 35 | Al2O3 | 156 | isobutanol | 3.50 | 1.3 | 10.4 | 5.0 | 6.4 | 68.2 | 91.2 |
| 36 | Al2O3 | 156 | isobutanol | 4.75 | 1.3 | 9.7 | 4.4 | 6.5 | 72.4 | 94.3 |
| 37 | Al2O3 | 156 | isobutanol | 6.34 | 1.4 | 8.9 | 4.0 | 6.3 | 74.2 | 94.8 |

As will be appreciated by one skilled in the art, the embodiments in the foregoing description of the specific embodiments will so fully reveal the general nature of the embodiments herein that others can, by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A continuous flow process for selectively making olefins in a reactor from energy dense alcohols comprising:
   providing a supply of oxygen gas;
   providing a supply of a 4-carbon liquid alcohol fuel selected from the group consisting of 1-butanols, 2-butanols, isobutanols, and mixtures thereof;
   atomizing said alcohol to form small droplets;
   evaporating said droplets to form a vapor; and reacting the vapor with the oxygen gas in the presence of a solid heterogeneous catalyst selected from the group consisting of $Rh/Al_2O_3$ foam and $Al_2O_3$ foam and mixtures thereof to produce a 4-carbon olefin selected from the group consisting of 1-butene, cis-2-butene, isobutene, trans-2-butene and mixtures thereof, wherein the contact time of the alcohol vapor with oxygen in the presence of the catalyst is between 145-550 ms.

2. The process of claim 1, wherein said catalyst is $Al_2O_3$ foam.

3. The process of claim 1, wherein said catalyst is $Rh/Al_2O_3$.

4. The process of claim 1, wherein the catalyst reaction temperature is from 300-600° C.

5. The process of claim 1, wherein said catalyst is both $Rh/Al_2O_3$ and $Al_2O_3$.

6. The process of claim 1, wherein the evaporation of the alcohol droplets to form a vapor is assisted by source of heat.

7. The process of claim 1, wherein the pressure at which the vapor is reacted is less than 10 psig.

8. The process of claim 1, wherein the alcohol vapor is mixed with the oxygen by one or more layers of uncoated alumina monolith foam.

9. The process of claim 1, wherein the alcohol droplets range from 4-25 microns.

10. The process of claim 9, wherein the droplets are approximately 6 microns.

11. The process of claim 1, where the oxygen gas is provided by air.

12. A process of claim 1 to produce a butene product from a butanol-containing feed stream, said process comprising contacting said feed stream with oxygen having an equivalence ratio range of 3-18 and a catalyst consisting essentially of alumina monolith foam with Rh gamma-alumina.

13. A process of claim 1 to produce trans-2-butene from a butanol-containing feed stream, said process comprising contacting said feed stream with oxygen having an equivalence ratio range of 0.15-18 and a catalyst consisting essentially of alumina monolith foam with Rh gamma-alumina.

14. A process of claim 1 to produce isobutylene from isobutanol, said process comprising contacting said isobutanol with oxygen having an equivalence ratio of approximately at least 0.176 and a catalyst consisting essentially of alumina on an alumina monolith foam.

15. A process of claim 1 to produce cis-2-butene and trans-2-butene from a butanol-containing feed stream, said process comprising contacting said feed stream with oxygen having an equivalence ratio of at least approximately 1.4 and a catalyst consisting essentially of alumina monolith foam with Rh gamma-alumina.

16. A process of claim 1 to produce isobutylene and 1-butene from a feed stream of isobutanol and 1-butanol, said process comprising contacting said feed stream with oxygen having an equivalence ratio of at least approximately 0.176 and a catalyst consisting essentially of alumina monolith foam with alumina.

17. A process of claim 3 having an equivalence ratio range of 5-18.

18. A process of claim 1 wherein the 4-carbon olefin is produced in a substantially complete combustion process having carbon selectivity of greater than 80% at equivalence ratios of 1 or less.

* * * * *